United States Patent
Liu et al.

(10) Patent No.: US 6,887,668 B2
(45) Date of Patent: May 3, 2005

(54) NUCLEIC ACID SEPARATION AND DETECTION BY ELECTROPHORESIS WITH A COUNTER-MIGRATING HIGH-AFFINITY INTERCALATING DYE

(75) Inventors: Ming-Sun Liu, Brea, CA (US); Fu-Tai-A Chen, Brea, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 172 days.

(21) Appl. No.: 10/126,195

(22) Filed: Apr. 19, 2002

(65) Prior Publication Data

US 2003/0198964 A1 Oct. 23, 2003

(51) Int. Cl.$^7$ .......................... C12Q 1/68; B01D 57/02
(52) U.S. Cl. .......................... 435/6; 204/450; 204/451; 204/456
(58) Field of Search .................... 204/450, 456, 204/451; 435/6

(56) References Cited

U.S. PATENT DOCUMENTS

| | | | |
|---|---|---|---|
| 5,110,424 A | 5/1992 | Chin | |
| 5,312,921 A | 5/1994 | Glazer et al. | |
| 5,734,058 A | 3/1998 | Lee | |
| 6,015,902 A | 1/2000 | Bieniarz et al. | |
| 6,045,995 A | 4/2000 | Cummins et al. | |
| 6,210,885 B1 | 4/2001 | Gjerde et al. | |
| 6,228,655 B1 | 5/2001 | Choi et al. | |

OTHER PUBLICATIONS http://www.cstl.nist.gov/biotech/strbase/pub_pres/Butler2004a_pre.pdf.*

Jarle Skeidsvoll, et al., "Analysis of Double–Stranded DNA by Capillary Electrophoresis with Laser–Induced Fluorescence Detection Using the Monomeric Dye SYBR Green I," Analytical Biochemistry, vol. 231, pp. 359–365, 1995.

Herbert E. Schwartz, et al., "Capillary Electrophoresis with Laser–Induced Fluorescence Detection of PCR Fragments Using Thiazole Orange," Analytical Chemistry, vol. 64, No. 15, pp. 1737–1740, Aug. 1, 1992.

Andras Guttman, et al., "Capillary Gel Affinity Electrophoresis of DNA Fragments," Analytical Chemistry, vol. 63, No. 18, pp. 2038–2042, Sep. 15, 1991.

Huan–Tsung Chang, et al., "Poly(ethyleneoxide) for High–Resolution and High–Speed Separation of DNA by Capillary Electrophoresis," Journal of Chromatography B, 669, pp. 113–123, 1995.

* cited by examiner

*Primary Examiner*—Jeffrey Fredman
(74) *Attorney, Agent, or Firm*—Hogan & Hartson, LLP

(57) ABSTRACT

The invention provides novel electrophoretic methods for high-resolution separation and high-sensitivity detection of nucleic acids. The methods involve the use of a high-resolution buffer and a counter-migrating high-affinity intercalating dye in an electrophoresis system to achieve superior separation and detection of nucleic acids. A kit for separation and detection of nucleic acids in a sample by electrophoresis is also provided. The kit comprises a gel buffer containing a high-resolution intercalating dye with a resolution of at least 2.0 between the 271-bp and 282-bp φX 171 HAIII nucleic acid fragments nucleic acid fragments; and a high-affinity intercalating dye having a positive charge and DNA affinity constant of at least $10^6 M^{-1}$.

22 Claims, 3 Drawing Sheets

NUCLEIC ACID SEPARATION AND DETECTION BY ELECTROPHORESIS WITH A COUNTER-MIGRATING HIGH-AFFINITY INTERCALATING DYE

FIELD OF THE INVENTION

The invention relates generally to the separation and detection of nucleic acids by electrophoresis. Specifically, the present invention relates to the electrophoresis with a counter-migrating intercalating dye.

BACKGROUND OF THE INVENTION

Various methods of separating and detecting deoxyribonucleic acids (DNA) from liquid biological samples are known in the art. One such technique, electrophoresis, involves the migration of charged electrical species when dissolved, or suspended, in an electrolyte through which an electric current is passed. Various conventional forms of electrophoresis are known including free zone electrophoresis, gel electrophoresis, isoelectric focusing, isotachophoresis, and capillary electrophoresis.

Traditionally, the separation and identification of nucleic acids have been accomplished by gel electrophoresis on polymer gels, such as agarose gels or polyacrylamide gels. Since polymer gels can be prepared in various types and sizes and their porosity can also be varied, polymer gels have a wide application. However, due to the instability over time, irreproducibility in the polymerization processes, the fragile nature of the medium, and post-separation detection, gel electrophoresis is generally not suitable for large-scale and high-speed applications (H.-T. Chang and E. S. Yeung, *J. Chromatogr. B* (1995) 669, 113).

Capillary electrophoresis (CE) represents a significant improvement in electrophoretic analysis of nucleic acids. For example, because CE is performed in very small diameter tubing (typically 50–100 $\mu$m) which results in reduced local Joule heating, electrical fields 10- to 100-fold greater than those used in conventional electrophoretic systems can be applied. This affords very high speed runs, improved resolution, and high reproducibility. Also, CE lends itself to on-column detection means including ultraviolet (UV) spectroscopy, amperometric measurement, conductivity measurement, laser-induced fluorescence detection (LIF) or thermo-optical detection. Additionally, CE is well suited for automation, since it provides convenient on-line injection, detection, and real-time data analysis.

Due to the small size of sample volumes injected in a typical CE analysis, the practical application of CE is highly dependent on sensitive detection systems (J. Skeidsvoll and P. M. Ueland, *Analytical Biochemistry*, (1995) 231, 359–365). There have been several reports of high sensitivity of DNA analysis by CE-LIF when fluorescent intercalating dyes or intercalators are used. Intercalators are planar molecules which interpose between base pairs in nucleic acids or similar structures. The fluorescence of the intercalators increases several-fold upon binding to DNA or RNA, thereby enabling the detection of small amounts of nucleic acids. (U.S. Pat. No. 5,734,058).

Ethidium Bromide (EB) is the most commonly used DNA intercalator, both in gel and capillary electrophoresis. In addition to its fluorescent properties, EB has been reported to provide high CE resolution of double-stranded DNA (dsDNA) (Id.; H.-T. Chang and E. S. Yeung, supra). High-resolution CE separations achieved with EB have been attributed to a reduction in the electrophoretic mobility of DNA when EB-DNA complex is formed. This mobility reduction increases with increasing molecular weight of the DNA (A. Guttman and N. Cooke, *Anal. Chem.* (1991) 63, 2038–2042). However, because EB binds relatively weakly to DNA ($K_{diss}=10^{-6}$ M$^{-1}$), the sensitivity of the DNA detection with EB is low. Generally, the detection limit is about 1 ng of double-stranded DNA (dsDNA) in 1 mm×5 mm band on a gel (U.S. Pat. No. 5,312,921).

Recently, an asymmetric cyanine dye, thiazole orange (TO; 4-[3-methyl-2,3-dihydro-(benzo-1,3-thiazole)-2-ethylidene]-quinolinium iodide) has been suggested as an alternative to EB (U.S. Pat. No. 5,312,921). Although this dye has a higher affinity to DNA and gives a 10-fold higher sensitivity than EB (Skeidsvoll & Ueland, supra), TO does not provide the same DNA separation performance as EB. For example, while the concentration of EB does not affect DNA separation, the quality of DNA separation is very sensitive to DNA-to-dye ratio when TO is used. It has been reported that DNA peak shape greatly deteriorates when DNA-to-dye ratio falls outside of the 9:1 ratio. Consequently, broad peaks and relatively low peak heights are observed when TO is used. One possible explanation for broad peaks is that TO not only intercalates but also binds to the separated DNA strands. Also, an excess of TO may be destabilizing to the DNA double helix, which results in broad peaks (H. E. Schwartz and K. J. Ulfelder, *Anal. Chem.* 1992, 64, 1737–1740).

Since the discovery of TO as a nucleic acid dye, several improvements to TO and its trimethine homologs have been developed to provide dyes with tighter binding to DNA and greater water solubility (U.S. Pat. No. 5,321,130 and U.S. Pat. No. 5,312,921). These dyes generally involve a modification to the quinolinium portion of the dye and are fairly expensive.

In summary, some conventional intercalating dyes, such as EB, provide a high DNA resolution but have a low affinity and low DNA detection sensitivity. On the other hand, other conventional intercalating dyes, such as TO, provide a high sensitivity of detection but do not provide desirable resolution. Accordingly, a continued interest exists in developing high resolution/high sensitivity techniques for detecting DNA in a sample, particularly where DNA is present in an extremely low concentration.

SUMMARY OF THE INVENTION

In view of the above-noted shortcomings of the conventional electrophoresis systems, it is an object of the present invention to provide high-resolution/high sensitivity electrophoretic methods for separating and detecting nucleic acids. It is particularly desirable to provide such a method which can be carried out in a capillary electrophoresis format.

These and other objects are achieved in the present invention by providing an electrophoresis system in which nucleic acids migrate from anode to cathode, while a high-affinity intercalating dye migrates in the opposite direction. Accordingly, one aspect of the present invention is directed to a method for separating and detecting nucleic acids contained in a sample by electrophoresis. The method comprises:

(a) providing an electrophoresis system having an anode end and a cathode end;

(b) loading the sample to the system from the cathode end;

(c) separating the nucleic acids contained in the sample by moving the nucleic acids in the presence of a high-resolution buffer from the cathode end toward the anode end by applying a voltage therebetween, wherein the high-resolution buffer provides a resolution of at least 2.0 between the 271-bp and 282-bp φX 171 HAIII nucleic acid fragments;

(d) loading a high-affinity intercalating dye into the system from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and (e) detecting the complexes.

The high-affinity intercalating dye may be selected from a group consisting of Thiazole Orange (TO), SYBR Green I, TO-PRO-1 iodide, TO-PRO-3 iodide, and TO-PRO-5 iodide (Molecular Probes; www.probes.com). The high-resolution buffer may comprise a high-resolution intercalating dye, wherein the high-resolution dye provides a resolution of at least 2.0 between the 271-bp and 282-bp φX 171 HAIII nucleic acid fragments. In one embodiment, the high-resolution dye is selected from a group consisting of Ethidium Bromide (EB), Propidium Iodide (PI), and Acidine Orange (HCl salt).

Another aspect of the present invention includes a method for separating and detecting nucleic acids contained in a sample by Capillary Electrophoresis (CE). The method comprises:

(a) providing a capillary tube having an anode end and a cathode end, wherein the capillary tube is filled with a high-resolution buffer with a resolution of at least 2.0 between the 271-bp and 282-bp φX 171 HAIII nucleic acid fragments;

(b) loading the sample into the capillary tube from the cathode end;

(c) separating the nucleic acids contained in the sample by applying a voltage between the anode and the cathode to move the nucleic acids from the cathode end toward the anode end in the presence of the high-resolution buffer;

(d) loading a high-affinity intercalating dye into the capillary tube from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and (e) detecting the complexes.

Still another aspect of the present invention is directed to a method for separating and detecting nucleic acids contained in a sample by CE with Laser-Induced Fluorescence Detection (CE-LIF) with multiple intercalating dyes. The method comprises:

(a) providing a capillary tube having an anode end and a cathode end, wherein the capillary tube is filled with a gel buffer comprising a high-resolution intercalating dye with a resolution of at least 2.0 between the 271-bp and 282-bp φX 171 HAIII nucleic acid fragments;

(b) loading the sample into the capillary tube from the cathode end;

(c) separating the nucleic acids contained in the sample by applying a voltage between the anode and the cathode to move the nucleic acids from the cathode toward the anode in the presence of the high-resolution buffer;

(d) loading a high-affinity intercalating dye into the capillary tube from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and (e) detecting the complexes.

In another aspect, the present invention provides a kit for the separation and detection of nucleic acids in a sample by electrophoresis. The kit comprises:

a gel buffer containing a high-resolution intercalating dye with a resolution of at least 2.0 between the 271-bp and 282-bp φX 171 HAIII nucleic acid fragments; and a high-affinity intercalating dye having a positive charge and DNA affinity constant of at least $10^6 M^{-1}$.

The present invention offers many economical and technical advantages over the conventional methods. The present invention allows the combination of the high resolution of nucleic acid separation with high detection sensitivity and reliability. Additionally, the methods of the present invention do not require any new equipment and can be used with any available electrophoresis systems. For example, the methods of the present invention may be used in connection with commercially available CE systems such as, but not limited to, CEQ™ 2000 DNA Analysis System, P/ACE™ MDQ Capillary Electrophoresis System, Paragon CZE® 2000 Capillary Electrophoresis System (Beckman Coulter, Inc., Fullerton, Calif.), ABI's Prism 310 genetic analyser, 3100 genetic analyser, 3700 DNA analyser (http://home.applied biosystems.com), Agilent 2100 Bioanalyzer (www.agilent.com).

Also, because a system of high-resolution buffer and a high-affinity dye is used, a broad range of available and newly developed high-affinity intercalating dyes can be utilized regardless of their resolving power in electrophoresis. Consequently, the sensitivity and resolution of this system can be easily adopted to address demands of various applications.

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope.

DETAILED DESCRIPTION OF THE INVENTION

This invention provides novel electrophoretic methods for high-resolution separation and high-sensitivity detection of nucleic acids. These novel methods are based on an unexpected discovery that by utilizing a system of a high-resolution buffer and a counter-migrating high-affinity intercalating dye, superior electrophoretic separation and the detection of nucleic acids can be achieved.

Accordingly, one aspect of the present invention provides a method for separating and detecting nucleic acids contained in a sample by electrophoresis. The method comprises:

(a) providing an electrophoresis system having an anode end and a cathode end;

(b) loading the sample to the system from the cathode end;

(c) separating the nucleic acids contained in the sample by moving the nucleic acids in the presence of a high-resolution buffer from the cathode end toward the anode end by applying a voltage therebetween, wherein the high-resolution buffer provides a resolution of at least 2.0 between the 271-bp and 282-bp φX 171 HAIII nucleic acid fragments;

(d) loading a high-affinity intercalating dye into the system from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and (e) detecting the complexes.

The electrophoresis system of the present invention is not limited to any particular type. Essentially, the above-described method is applicable to any type of electrophoresis, including, but not limited to, free zone electrophoresis, gel electrophoresis, isoelectric focusing, isotachophoresis, and CE. The electrophoresis system of the present invention can be any electrophoretic apparatus. For example, the methods of the present invention may be used in connection with commercially available CE systems such as, but not limited to, CEQ™ 2000 DNA Analysis System, P/ACE™ MDQ Capillary Electrophoresis System, and Paragon CZE® 2000 Capillary Electrophoresis System (Beckman Coulter, Inc., Fullerton, Calif.), ABI's Prism 310 genetic analyser, 3100 genetic analyser, 3700 DNA analyser (http://home.applied biosystems.com), Agilent 2100 Bioanalyzer (www.agilent.com). Typically, the applied voltage gradient in the electrophoretic apparatus is in the range from 100 to 1000 V/cm.

In the present invention, in addition to a mixture of nucleic acids, the sample may include other ingredients such as buffers, solvents, restriction enzymes, and other reagents used in isolation of nucleic acids and/or preparing the sample. This invention does not place any limitation on the number and type of such additional ingredients. Also, in the present invention, the PCR reaction products can be directly introduced into the electrophoresis system without any pre-treatment of the DNA samples. For example, ethanol precipitation, redissolve in formamide and heat treatment of PCR reaction products to yield single-stranded DNA sample are not required.

Nucleic acids can derive from a variety of sources, such as viral, bacterial and eukaryotic DNAs, and RNAs. Alternatively, nucleic acids may be a synthetic oligomeric species. Nucleic acids may be selected from a group consisting of nucleic acid fragments, amplified DNA, cDNA, single-stranded DNA, double-stranded DNA, peptide nucleic acid (PNA), RNA, and mRNA. In one embodiment, the nucleic acid fragments are in the size range from 10 to 100,000 basepairs. The amount of nucleic acids will be generally within conventional amounts used in electrophoresis.

As defined herein, an "intercalating dye" is a generally planar, aromatic, ring-shaped chromophore molecule which binds to nucleic acids in a reversible, non-covalent fashion, by insertion between the base pairs of the double helix. Preferred intercalating dyes in the present invention include fluorescent dyes. Numerous intercalating dyes are known in the art. Some non-limiting examples include PICO GREEN (P-7581, Molecular Probes), EB (E-8751, Sigma), propidium iodide (P-4170, Sigma), Acridine orange (A-6014, Sigma), 7-aminoactinomycin D (A-1310, Molecular Probes), cyanine dyes (e.g., TOTO, YOYO, BOBO, and POPO), SYTO, SYBR Green I, SYBR Green II, SYBR DX, OliGreen, CyQuant GR, SYTOX Green, SYTO9, SYTO10, SYTO17, SYBR14, FUN-1, DEAD Red, Hexidium Iodide, Dihydroethidium, Ethidium Homodimer, 9-Amino-6-Chloro-2-Methoxyacridine, DAPI, DIPI, Indole dye, Imidazole dye, Actinomycin D, Hydroxystilbamidine, and LDS 751 (U.S. Pat. No. 6,210,885).

Intercalating dyes differ in their affinity toward DNA. For the purposes of the present invention, a "high-affinity intercalating dye" is an intercalating dye with a DNA affinity constant of at least $10^6 M^{-1}$. High-affinity intercalating dye of the present invention is also required to have a positive charge in order to ensure its migration from the anode to the cathode during electrophoresis. In one embodiment, the high-affinity intercalating dye is selected from a group consisting of Thiazole Orange (TO), SYBR Green I, TO-PRO-1 iodide, TO-PRO-3 iodide, and TO-PRO-5 iodide (Molecular Probes; www.probes.com).

A high-affinity intercalating dye may be loaded into the electrophoresis system before the nucleic acid separating step (c). Alternatively, a high-affinity intercalating dye may be loaded into the electrophoresis system after the nucleic acid separating step (c), but before the separated nucleic acids either reach a detection device or exit the separation medium (such as gel) at the anode end of the electrophoresis device.

The high-resolution buffer of the present invention may be any solution or gel that provides the desired nucleic acid resolution of at least 2.0 between the 271-bp and 282-bp φX 171 HAIII nucleic acid fragments. Examples of suitable high-resolution buffers include, but are not limited to, tris-borate-EDTA (TBE) buffer, tris-acetate-EDTA (TAE), and MOPS-tris. In one embodiment, the high-resolution buffer also comprises an intercalating dye. The intercalating dye of the high-resolution buffer is preferably a high-resolution intercalating dye. For the purposes of the present invention, a "high-resolution intercalating dye" is an intercalating dye that provides a resolution of at least 2.0 between the 271-bp and 282-bp φX 171 HAIII nucleic acid fragments. For example, the high-resolution dye may be EB, Propidium Iodide (PI), or Acidine Orange.

In one embodiment, nucleic acids are stained with high-resolution intercalating dye prior to electrophoresis. A preferred ratio of dye to DNA is about two molecules of dye per 10 base pairs. In another embodiment, a high-resolution intercalating dye is included in the chromatographic mobile phase. Advantageously, many such dyes (e.g., EB) have little or no intrinsic fluorescence and actually exhibit fluorescence only when intercalated into a polynucleotide.

After the voltage is applied between cathode and anode, nucleic acids separate in a high-resolution buffer while moving toward the anode. At the same time, the molecules of the high-affinity intercalating dye migrate in the opposite direction, from the anode to the cathode, due to their positive charge. Once the molecules of the counter-migrating high-affinity dye come into contact with the separated nucleic acids, they form complexes with nucleic acids. Preferably, the absolute value of the DNA charge is larger than that of the high-affinity intercalating dye, so that the overall charge of the new complexes is negative and the complexes move toward the anode.

In embodiments where the high-resolution buffer comprises a high-resolution intercalating dye, after the voltage is applied between the cathode and the anode, nucleic acids form complexes with the molecules of the high-resolution intercalating dye. These complexes carry a negative charge and migrate in the direction from the cathode to the anode. At the same time, the molecules of the high-affinity intercalating dye migrate in the opposite direction, from the anode to the cathode, due to their positive charge. Once the molecules of the counter-migrating high-affinity dye come into contact with the separated complexes of the nucleic acids with the high-resolution dye, the molecules of the high-affinity dye replace the molecules of the high-resolution dye. To ensure that such a substitution takes an effect, the high-affinity dye should have a higher DNA affinity than the high-resolution dye. As a result of the substitution, new negatively charged complexes between the nucleic acids and the molecules of the high-affinity dye form and migrate toward the anode.

Any conventional detection system may be employed for detecting complexes of high-affinity intercalating dye with the separated nucleic acids. Examples of such detection systems include, but are not limited to, laser-induced fluorescent (LIF) detection and UV detection at 254 nm. Depending on the particular high-affinity intercalating dye employed, the excitation light will be chosen to be within a major absorption band of the dye. For example, when TO or SYBR Green I high-affinity intercalating dyes are used, an argon-ion laser may be utilized to induce fluorescence, and the fluorescence may be detected at 520 nm.

In one embodiment of the invention, the separation and the detection of nucleic acids is carried out by capillary electrophoresis (CE). As used herein, the term "capillary electrophoresis" is used in its normal sense and indicates electrophoretic separation performed in relatively low volume systems, such as narrow bore plastic tubes, glass capillaries, or thin fluid films between parallel plates.

In a preferred embodiment, capillary tubes (or capillaries) are used. Capillary tubes are typically hollow tubes which are capable of retaining by itself the aqueous solution used for electrophoresis. Normally, this means tube diameters of 5–500 µm, the exact limits being dependent on surface characteristics and constituents present in the solution. The length of CE capillaries may vary within wide limits but in most cases they should be within the range 5–100 cm. Commercially available or custom-made capillary tubes (or columns) may be used in the present invention. For example, capillary tubes of various sizes may be purchased from Polymicro Technology (Tucson, Ariz.). In one embodiment described in Examples 1 and 2, the capillary tube made by Polymicro Technology (Tucson, Ariz.) has an internal diameter of 100 µm and the length of 27 cm.

Although many materials may be used to form capillaries, typically, fused silica capillaries are used. Usually, fused silica capillaries are covered with an external protective coating to give them increased mechanical strength as bare fused silica is extremely fragile. A small portion of this coating is removed to form a window for detection purposes. The window is aligned in the optical center of the detector. The inner surface of the capillary can be chemically modified by covalently binding (coating) different substances onto the capillary wall. These coatings are used for a variety of purposes, such as to reduce sample adsorption or to change the ionic charge on the capillary wall. However, it should be understood that this invention is not limited to any particular type of capillaries. For example, in one embodiment, polyvinyl alcohol (PVA)—coated silica capillary is used.

In a CE separation, the capillary is filled with buffer and each end is immersed in a vial of the same buffer. A sample of analyte is injected at one end, either by electrokinesis or by pressure, and an electrical field of 100 to 700 volts/centimeter is applied across the capillary. As the analyte mixture migrates through the capillary due to the applied electrical field, differing electrophoretic mobilities drive each of the components into discrete bands. At the other end of the capillary, each of the separated analytes is detected and quantified. In the present invention, CE may be performed in this or any other convenient manner. Thus, the present invention advantageously allows the use of conventional CE formats and does not require any modifications of the standard CE equipment.

The amount of nucleic acids will be conventional amounts employed for electrophoresis ranging from 0.1 to 100 µg/ml. In one embodiment, a sample with 10 µg/ml of φX-174 HaIII fragments (Sigma Co., St. Louis, Mo.) is used.

The detection of nucleic acids separated by CE may be achieved by any of the known conventional techniques, such as LIF and UV detection at 254 nm (a substantially reduced sensitivity). In preferred embodiments, the detection of hybridized moieties is accomplished by on-column LIF detection techniques.

Accordingly, another aspect of the present invention provides a method for separating and detecting nucleic acids contained in a sample by CE, comprising:

(a) providing a capillary tube having an anode end and a cathode end, wherein the capillary tube is filled with a high-resolution buffer with a resolution of at least 2.0 between the 271-bp and 282-bp φX 171 HAIII nucleic acid fragments;

(b) loading the sample into the capillary tube from the cathode end;

(c) separating the nucleic acids contained in the sample by applying a voltage between the anode and the cathode to move the nucleic acids from the cathode end toward the anode end in the presence of the high-resolution buffer;

(d) loading a high-affinity intercalating dye into the capillary tube from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and (e) detecting the complexes.

The high-resolution buffer for use in CE may be any buffer or gel that provides the desired nucleic acid resolution of at least 2.0 between the 271-bp and 282-bp φX 171 HAIII nucleic acid fragments In preferred embodiments, the electrophoresis capillary is filled with a high-resolution gel. For example, in one embodiment polyacrylamide replaceable gel or fixed gel is used. In another embodiment, linear polyacrylamide is used as the high-resolution gel.

The high-resolution buffer or gel may also comprise a high-resolution intercalating dye. For example, the high-resolution dye may be EB, Propidium Iodide (PI), or Acidine Orange. In one embodiment discussed in Examples 1 and 2, the capillary tube is filled with a polyethyleneoxide (PEO) gel mixed with EB (final concentration of 30 µM).

Any high-affinity intercalating dye that is positively charged and has a DNA affinity constant of at least $10^6 M^{-1}$ may be used in the present invention. For example, a high-affinity intercalating dye may be selected from a group consisting of TO, SYBR Green I, TO-PRO-1 iodide, TO-PRO-3 iodide, and TO-PRO-5 iodide (Molecular Probes: www.probes.com).

The high-affinity intercalating dye may be loaded into the electrophoresis system (capillary) before the nucleic acid separating step (c). Alternatively, a high-affinity intercalating dye may be loaded into the electrophoresis system after the nucleic acid separating step (c), but before the separated nucleic acids either reach a detection device or exit the capillary at the anode end of the electrophoresis device.

In one embodiment, the capillary is filled with buffer and one end of the capillary is immersed in a cathode reservoir and the second end of the capillary is immersed in an anode reservoir. Both reservoirs are filled with the same buffer. Then, the loading step (d) may comprise adding the high-affinity intercalating dye into the filled anode reservoir or premixing it with the anode buffer prior to the filling of the anode reservoir. Once voltage is applied between the cathode and the anode, the positively charged high-affinity dye will enter the capillary and will move toward the cathode. Alternatively, the high-affinity intercalating dye may be injected directly into the anode end of the capillary.

While any high-resolution buffer may be used in accordance with the teachings of the present invention, in one embodiment, the high-affinity buffer comprises a high-affinity intercalating dye. Accordingly, the present invention provides a method for separating and detecting nucleic acids contained in a sample by CE-LIF with multiple intercalating dyes. The method comprises:

(a) providing a capillary tube having an anode end and a cathode end, wherein the capillary tube is filled with a gel buffer comprising a high-resolution intercalating dye with a resolution of at least 2.0 between the 271-bp and 282-bp ϕX 171 HAIII nucleic acid fragments;

(b) loading the sample into the capillary tube from the cathode end;

(c) separating the nucleic acids contained in the sample by applying a voltage between the anode and the cathode to move the nucleic acids from the cathode toward the anode in the presence of the high-resolution buffer;

(d) loading a high-affinity intercalating dye into the capillary tube from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and (e) detecting the complexes.

Figure 1:
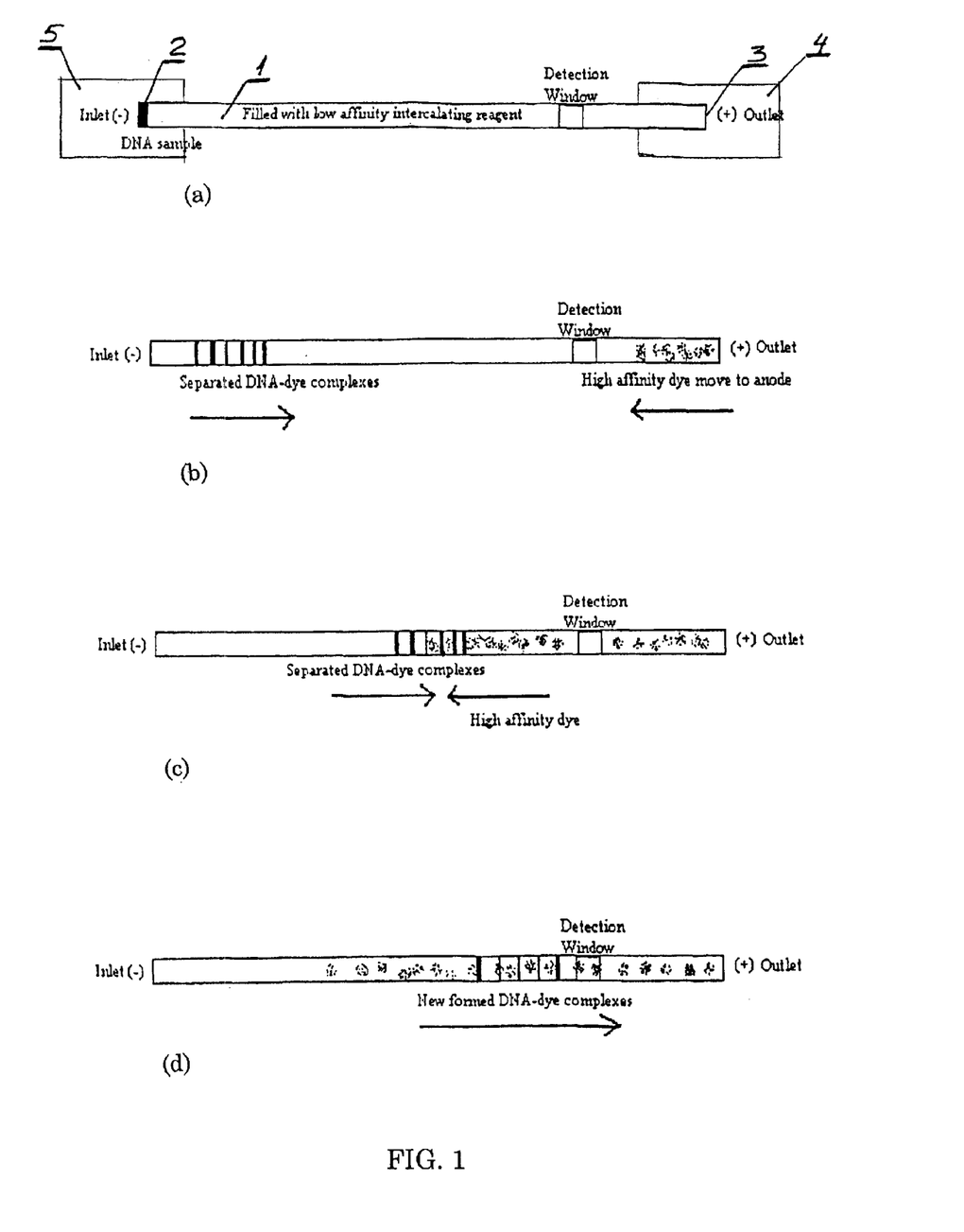
FIG. 1 is a diagram illustrating the separation and detection of nucleic acids by CE-LIF using two intercalating dyes, of which one is a high-resolution intercalating dye and the other is a high-affinity intercalating dye.

FIG. 1 illustrates such a method in accordance with one embodiment of the present invention. As shown in FIG. 1a, the capillary 1, with an inlet (cathode end) 2 and outlet (anode end) 3, was filled with a buffer containing low-affinity, high-resolution intercalating dye (HRID). The outlet of the capillary is in the fluid communication with the outlet (anode) reservoir 4. The inlet of the capillary is in the fluid communication with the inlet (cathode) reservoir 5. The anode reservoir was filled with the outlet buffer comprising high-affinity intercalating dye (HAID). A nucleic acid sample was injected into the capillary through inlet 2.

After the voltage was applied between the cathode and the anode, DNA-HRID complexes were formed and moved toward the anode. At the same time, the molecules of HAID migrated in the opposite direction, from the anode to the cathode, due to their positive charges (FIG. 1b).

Once the counter-migrating HAID molecules came into contact with the separated DNA-HRID complexes, they replaced HRID in the DNA complexes due to their higher DNA affinity, as compared to that of HRID. As a result, new DNA-HRID complexes were formed (FIG. 1c).

Because the absolute value of the DNA charge was larger than that of HAID, the overall charge of the new complexes was negative and the complexes moved toward the anode. Once these newly formed complexes reached the detection window, they were detected by one of conventional detection methods (FIG. 1d).

Detected nucleic acid bands may be extracted and isolated from the intercalated fluorescent dye, when required by the application. Any standard methods can be used for such extraction. Such methods are known to those skilled in the art and will not be discussed here.

In another aspect, the present invention provides a kit for the separation and the detection of nucleic acids in a sample by electrophoresis. The kit comprises:

a gel buffer containing a high-resolution intercalating dye with a resolution of at least 2.0 between the 271-bp and 282-bp ϕX 171 HAIII nucleic acid fragments; and a high-affinity intercalating dye having a positive charge and DNA affinity constant of at least $10^6 M^{-1}$.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Example 1

CE Setup

Capillaries (Polymicro Technology, Tucson, Ariz.) with 100 μm internal diameter and 27 cm length were used in the following studies. The capillaries were coated with polyvinyl alcohol (PVA) before use. EB, SYBR Green I, and TO were purchased from Molecular Probes (Eugene, Oreg.).

The gel matrix was prepared with polyethyleneoxide (PEO) purchased from Aldrich Co. (Milwaukee, Wis.). Briefly, the PEO gel was prepared as follows. 2.5 g of PEO (average molecular weight 4,000,000) and 2 g PEO (average molecular weight 900,000) were added slowly (overnight) and with stirring to 445 ml of water at room temperature. Then, 50 ml of 250 mM MOPS-Tris pH 7.55 and 325 μl of 10% NaN3 were added to the obtained solution. The resulting gel was stored at room temperature.

The rinsing buffer was prepared by mixing PEO gel with EB (final concentration was 30 μM). The outlet buffer was prepared by mixing PEO gel with SYBR Green I (1:500 dilution). In another experiment, the outlet buffer was prepared by mixing PEO gel with TO (final concentration was 3 μg/ml).

DNA sample was ϕX 174/HaIII ϕx-174 HaIII fragments (Sigma Co., St. Louis, Mo.).

The injected concentration of DNA was 10 μg/ml. The injection was performed at 5.4 kV for 10 seconds. The rinsing buffer was prepared by mixing PEO gel with EB (final concentration was 30 μm). The outlet buffer was prepared by mixing PEO gel with SYBR Green I (1:500 dilution). In another experiment, the outlet buffer was prepared by mixing PEO gel with TO (final concentration was 3 μg/ml). Applied voltage gradient was is in the range of 100 v/cm to 400 v/cm.

Example 2

DNA Analysis by CE-LIF Using Two Intercalating Dyes

The capillary was filled with the gel buffer containing the PEO gel and EB. The outlet electrode vial (anode) was filled with the outlet buffer comprising the PEO gel and SYBR Green I or TO. The DNA sample was injected into the capillary from the cathode. After the voltage was applied between the cathode and the anode, the DNA-EB complexes were formed and moved toward the anode. At the same time, the SYBR Green I or TO molecules moved in the opposite direction from the anode to the cathode, due to their positive charges.

Figure 2:
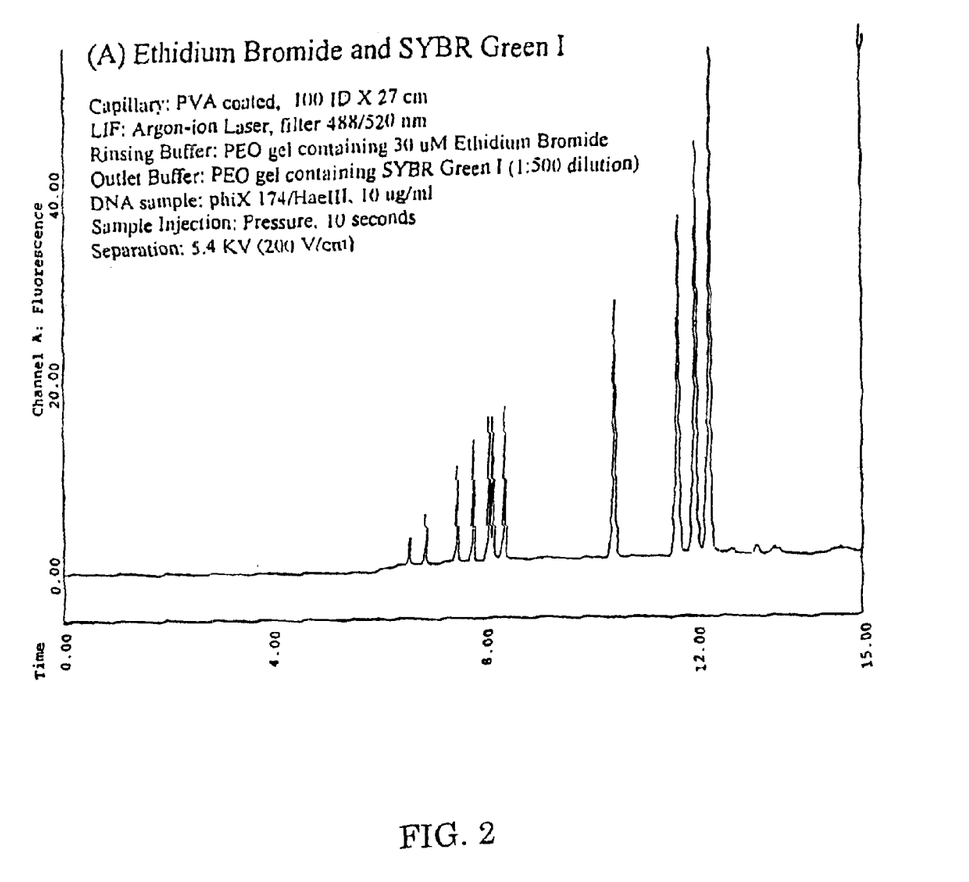
FIG. 2 shows an electropherogram of DNA analysis by CE-LIF with EB and SYBR Green I intercalating dyes.

Once the counter-migrating SYBR Green I or TO molecules came into contact with the separated DNA-EB complexes, they replaced the EB in the DNA complexes due to their higher DNA affinity, as compared to that of the EB. As a result, new DNA-SYBR Green I or DNA-TO complexes were formed. Because the absolute value of the DNA charge was larger than that of SYBR Green I and TO, the overall charge of the new complexes was negative and the complexes moved toward the anode. Once these newly formed complexes reached the detection window, the dyes were excited by an Argon-ion laser and detected at the wavelength of 520 nm. The results of CE-LIF with EB and SYBR Green I is shown in FIG. 2. The results of combining CE-LIF with EB and TO are presented in FIG. 3.

Figure 3:
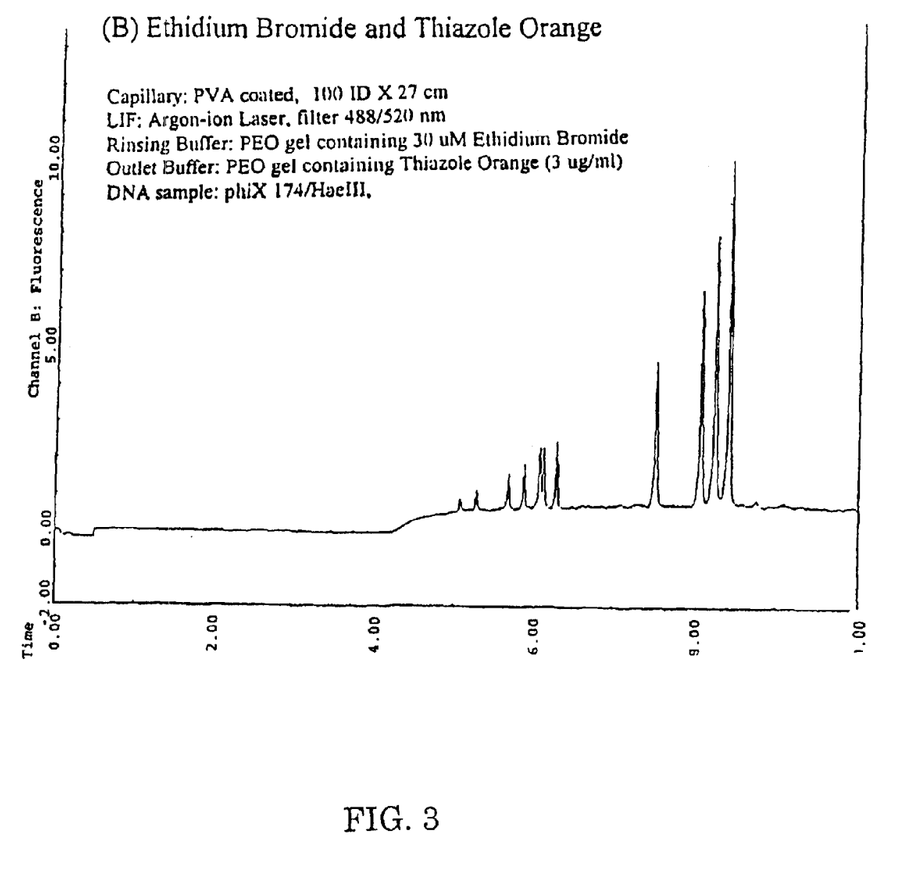
FIG. 3 shows an electropherogram of DNA analysis by CE-LIF with EB and TO intercalating dyes.

The results shown in FIGS. 2 and 3 demonstrate that by using a high resolution intercalating dye (e.g. EB) to separate nucleic acids and a high-affinity intercalating dye (e.g., SYBR Green I or TO) to detect the separated nucleic acids, the present invention achieves a rapid high-resolution/high-sensitivity analysis of nucleic acids.

What is claimed is:

1. A method for separating and detecting nucleic acids contained in a sample by electrophoresis, comprising:
    (a) providing an electrophoresis system having an anode end and a cathode end;
    (b) loading the sample to the system from the cathode end;
    (c) separating the nucleic acids contained in the sample by moving the nucleic acids in the presence of a high-resolution buffer from the cathode end toward the anode end by applying a voltage therebetween, wherein the high-resolution buffer comprises a high-resolution intercalating dye, wherein the high-resolution intercalating dye is selected from a group consisting of Ethidium Bromide (EB), Propidium Iodide (PI), and Acidine Orange (HCl salt);
    (d) loading a high-affinity intercalating dye into the system from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and
    (e) detecting the complexes.

2. The method of claim 1, wherein the high-affinity intercalating dye is selected from a group consisting of Thiazole Orange (TO), SYBR Green I, TO-PRO-1 iodide, TO-PRO-3 iodide, and TO-PRO-5 iodide.

3. The method of claim 1, wherein the high-affinity intercalating dye is loaded into the electrophoresis system before the nucleic acid separating step (c).

4. The method of claim 1, wherein the high-affinity intercalating dye is loaded into the electrophoresis system during the nucleic acid separating step (c).

5. The method of claim 1, wherein the nucleic acids are selected from a group consisting of nucleic acid fragments, amplified DNA, cDNA, single-stranded DNA, double-stranded DNA, PNA, RNA, and mRNA.

6. The method of claim 5, wherein the nucleic acid fragments are in the size range from 10 bp to 100 kbp.

7. The method of claim 1 wherein the detecting step is performed using laser-induced fluorescent (LIF) detection or UV detection at 254 nm.

8. The method of claim 7, wherein an argon-ion laser is used to induce fluorescence, and the fluorescence is detected at 520 nm.

9. the method of claim 1, wherein the electrophoresis system comprises a microcapillary tube filled with a high-resolution buffer.

10. The method of claim 9, wherein high-resolution buffer selected from a group consisting of tris-borate-EDTA (TBE) buffer, tris-acetate-edta (TAE), and MOPS-tris.

11. A method for separating and detecting nucleic acids contained in a sample by Capillary Electrophoresis, comprising:
    (a) providing a capillary tube having an anode end and a cathode end, wherein the capillary tube is filled with a high-resolution buffer, wherein the high-resolution buffer comprises a high-resolution intercalating dye, wherein the high-resolution intercalating dye is selected from group consisting of Ethidium Bromide (EB), Propidium Iodide (PI), and Acidine Orange (HCl salt);
    (b) loading the sample into the capillary tube from the cathode end;
    (c) separating the nucleic acids contained in the sample by applying a voltage between the anode and the cathode to move the nucleic acids from the cathode end toward the anode end in the presence of the high-resolution buffer;
    (d) loading a high-affinity intercalating dye into the capillary tube from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and
    (e) detecting the complexes.

12. The method of claim 11, wherein the high-affinity intercalating dye is selected from a group consisting of Thiazole Orange (TO), SYBR Green I, TO-PRO-1 iodide, TO-PRO-3 iodide, TO-PRO-5 iodide.

13. The method of claim 11, wherein the high-affinity intercalating dye is loaded into the capillary tube before the nucleic acid separating step (c).

14. The method of claim 11, wherein the high-affinity intercalating dye is loaded into the capillary tube during the nucleic acid separating step (c).

15. The method of claim 11, wherein the nucleic acids are selected from a group consisting of nucleic acid fragments, amplified DNA, cDNA, single-stranded DNA, double-stranded DNA, PNA, RNA, and mRNA.

16. The method of claim 15, wherein the nucleic acid fragments are in the size range from 10 bp to 100 kbp.

17. The method of claim 11, wherein the detecting step is performed using laser-induced fluorescent (LIF) detection or UV detection at 254 nm.

18. The method of claim 11, wherein an argon-ion laser is used to induce fluorescence, and the fluorescence is detected at 520 nm.

19. The method of claim 11, wherein the anode end of the capillary tube is in fluid communication with an anode reservoir and the cathode end of the capillary tube is in fluid communication with a cathode reservoir, wherein the capillary tube, the cathode reservoir and the anode reservoir are filled with the high-resolution buffer, and wherein the loading step (d) comprises adding the high-affinity intercalating dye into the anode reservoir.

20. The method of claim 11, wherein the high resolution buffer is selected from a group consisting of tris-borate-EDTA (TBE) buffer, tris-acetate-edta (TAE), and MOPS-tris.

21. A method for separating and detecting nucleic acids contained in a sample by CE-LIF with multiple intercalating dyes, comprising:

(a) providing a capillary tube having an anode end and a cathode end, wherein the capillary tube is filled with a gel buffer comprising a high-resolution intercalating dye, wherein the high-resolution intercalating dye is selected from a group consisting of Ethidium Bromide (EB), Propidium Iodide (PI), and Acidine Orange (HCl salt);

(b) loading the sample into the capillary tube from the cathode end;

(c) separating the nucleic acids contained in the sample by applying a voltage between the anode and the cathode to move the nucleic acids from the cathode toward the anode in the presence of the high-resolution buffer;

(d) loading a high-affinity intercalating dye into the capillary tube from the anode end, wherein the intercalating dye has a positive charge and DNA affinity constant of at least $10^6 M^{-1}$, and wherein the intercalating dye moves from the anode end toward the cathode end under the voltage applied therebetween, and forms complexes with the separated nucleic acids; and (e) detecting the complexes.

22. The method of claim 21, wherein the high-affinity intercalating dye is selected from a group consisting of Thiazole Orange (TO), SYBR Green I, TO-PRO-1 iodide, TO-PRO-3 iodide, and TO-PRO-5 iodide.

* * * * *

UNITED STATES PATENT AND TRADEMARK OFFICE
CERTIFICATE OF CORRECTION

PATENT NO. : 6,887,668 B2   Page 1 of 1
APPLICATION NO. : 10/126195
DATED : May 3, 2005
INVENTOR(S) : Liu et al.

It is certified that error appears in the above-identified patent and that said Letters Patent is hereby corrected as shown below:

Title Page, Item 57, line 10, "ΦX 171 HAIII" should read --ΦX 174 HaeIII--.

Column 2, line 54, "anode to cathode" should read --cathode to anode--.

Column 3:
Lines 3, 19-20, 31, and 55-56, "ΦX 171 HAIII" should read --ΦX 174 HaeIII--.

Column 4, line 11, "ΦX 171 HAIII" should read --ΦX 174 HaeIII--.

Column 5, line 9, "ΦX 171 HAIII" should read --ΦX 174 HaeIII--.

Column 6:
Lines 33-34 and 43, "ΦX 171 HAIII" should read --ΦX 174 HaeIII--.

Column 8:
Line 15, "ΦX-174 HaIII" should read --ΦX 174 HaeIII--.

Lines 29, and 47, "ΦX 171 HAIII" should read --ΦX 174 HaeIII--.

Column 9, lines 30-31, "ΦX 171 HAIII" should read --ΦX 174 HaeIII--.

Column 10:
Line 17, "ΦX 171 HAIII" should read --ΦX 174 HaeIII--.

Line 50, "DNA sample was ΦX 174/HaIII Φx-174 HaIII fragments" should read --DNA sample was ΦX 174 HaeIII fragments--.

Signed and Sealed this

Ninth Day of February, 2010

David J. Kappos
*Director of the United States Patent and Trademark Office*